Sept. 29, 1936. A. F J. BAUR Plant Pat. 198
CARNATION
Filed April 18, 1936
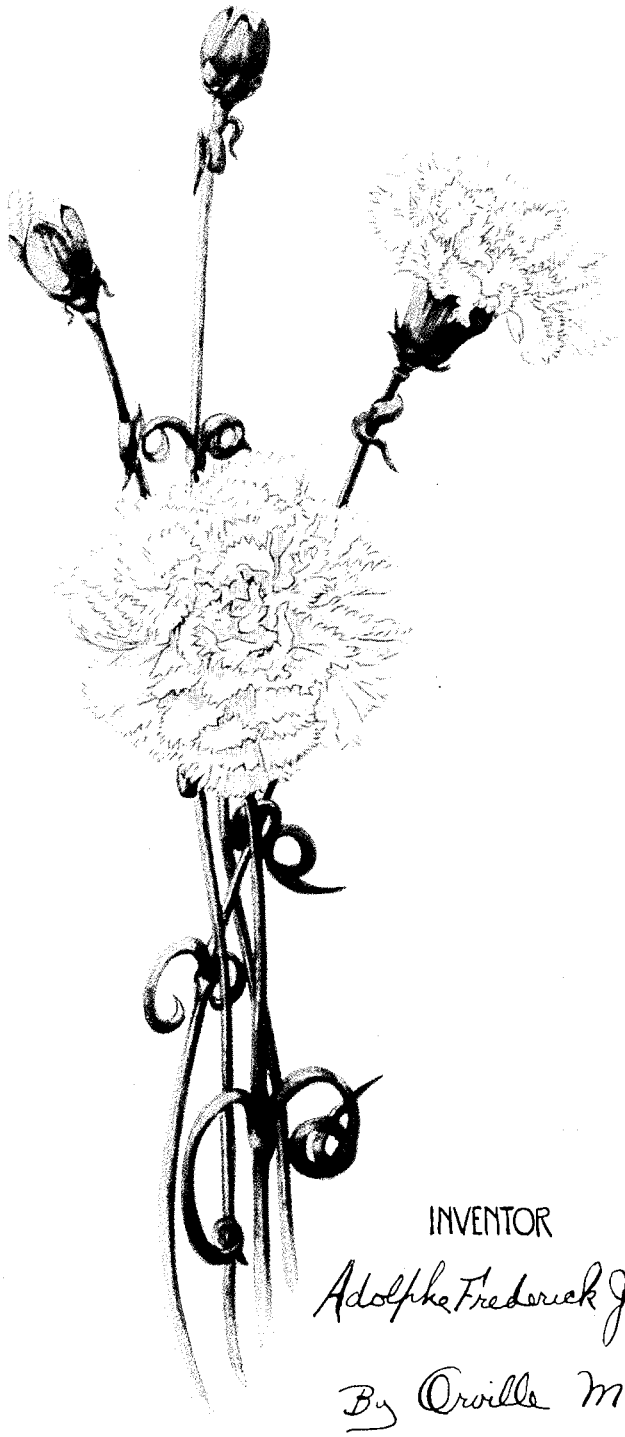
INVENTOR
Adolphe Frederick Jacob Baur
By Orville M. Kile
PLANT PATENT AGENT Patented Sept. 29, 1936

Plant Pat. 198

UNITED STATES PATENT OFFICE

198

CARNATION

Adolphe Frederick Jacob Baur, Indianapolis, Ind., assignor to Baur-Steinkamp and Company, Incorporated, Indianapolis, Ind.

Application April 18, 1936, Serial No. 75,187

1 Claim. (Cl. 47—60)

My present invention relates to improvements in pink carnations ordinarily known as greenhouse forcing carnations. The object of my invention is to provide a medium pink carnation without salmon tones; having a fuller form without a splitting calyx; with long, strong stems; of vigorous, disease-resistant growth; and of excellent keeping qualities.

This variety is a sport of Chief Kokomo and is the shade of the pink stripe in its parent variety. It also has the same strong, vigorous growth as the parent and is in fact very similar to it except as to color.

The original illustrations show in full natural color and approximately natural size, a full front view, a side view and two buds in different stages of opening, together with stems and foliage. It must be understood, however, that the artist cannot exactly duplicate the natural colors.

The following is a detailed description of this variety, and the color references are to Ridgway's Color Standards and Nomenclature.

*The plant*

*Growth habits.*—This variety is a strong and vigorous grower and is apparently resistant to diseases which commonly attack carnations. It propagates easily and blooms freely.

*Stems.*—The stems are long and strong; of an elm green color (Plate XVII) overlaid with a gray bloom.

*Foliage.*—Rather scarce; leaves of elm green color overlaid with gray bloom—moderately short and curled.

*Calyx.*—Rather long but exceptionally strong calyx which does not split. Color is biscay green (Plate XVII) at the top, diminishing to absinthe green (Plate XXXI) at the base, with light yellow lines rather close together extending vertically across the calyx.

*Bracts.*—Medium in length and much darker green than the calyx (approximately the same shade as the stems).

*The flower*

*Shape and size.*—Large, double and full, measuring from 3 to 4 inches across. In February in the vicinity of Indianapolis, the petals number from 43 to 45. High and well-filled center.

*Petals.*—Each petal is irregularly serrated and moderately crinkled.

*Styles.*—Two in number; curled tops; extending beyond stamens.

*Ovary.*—Pointed; large.

*Color.*—The color is not evenly distributed although the general color effect is between rose color and tyrian rose (Plate XII). There are some splashes or lines of a deeper shade approaching spinel red (Plate XXVI). The under side of petals is much lighter (Rose Pink, Plate XII). The absence of salmon hue is notable. Each petal has a considerable area of white at the base, running up in fine whitish lines or streaks or occasional splotches distributed over the surface but not in sufficient quantity to subtract from the general effect of solid rose color.

*Odor.*—Very fragrant with a decided cinnamon scent.

*Durability.*—Has extra good keeping qualities.

*Buds.*—Blunt and bulged, due to the large number of petals inclosed.

Having thus disclosed my invention, I claim:

The variety of carnation herein shown and described characterized particularly by its clear medium pink color as indicated, full petalage, nonsplitting calyx, vigorous growth habits, and excellent keeping qualities.

ADOLPHE FREDERICK JACOB BAUR.